(12) United States Patent
Baillet

(10) Patent No.: US 9,579,672 B2
(45) Date of Patent: Feb. 28, 2017

(54) FLUID OR POWDERY PRODUCT DISPENSING DEVICE

(71) Applicant: APTAR FRANCE SAS, Le Neubourg (FR)

(72) Inventor: Matthieu Baillet, Bonsecours (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 14/890,997

(22) PCT Filed: Jul. 4, 2014

(86) PCT No.: PCT/FR2014/051727
§ 371 (c)(1),
(2) Date: Nov. 13, 2015

(87) PCT Pub. No.: WO2015/001274
PCT Pub. Date: Jan. 8, 2015

(65) Prior Publication Data
US 2016/0082455 A1 Mar. 24, 2016

(30) Foreign Application Priority Data
Jul. 5, 2013 (FR) .................................... 13 56658

(51) Int. Cl.
*B05B 11/06* (2006.01)
*A61M 11/02* (2006.01)
*A61M 15/00* (2006.01)

(52) U.S. Cl.
CPC ........... *B05B 11/062* (2013.01); *A61M 11/02* (2013.01); *A61M 15/0028* (2013.01);
(Continued)

(58) Field of Classification Search
CPC .......... A61M 15/0028; A61M 15/0061; A61M 11/02; A61M 2205/073; A61M 2202/064;
(Continued)

(56) References Cited

U.S. PATENT DOCUMENTS

| 4,017,007 A | 4/1977 | Riccio |
| 6,877,672 B2 * | 4/2005 | Stihl ................. A61M 15/0028 222/82 |

(Continued)

FOREIGN PATENT DOCUMENTS

| EP | 0 575 239 A1 | 12/1993 |
| EP | 1 321 160 A2 | 6/2003 |

(Continued)

OTHER PUBLICATIONS

International Preliminary Report on Patentability dated Jan. 7, 2016 from the International Bureau in counterpart International Application PCT/FR2014/051727.

(Continued)

*Primary Examiner* — Kevin P Shaver
*Assistant Examiner* — Robert Nichols, II
(74) *Attorney, Agent, or Firm* — Sughrue Mion, PLLC

(57) ABSTRACT

A dispenser device for dispensing a fluid or powder composition, including a dispenser outlet, an air expeller, and a reservoir containing a dose of a composition. The reservoir includes an air inlet connected to the air expeller, and a composition outlet connected to the dispenser outlet. The air inlet includes a composition retainer member for retaining the composition in the reservoir until the composition is dispensed, and the composition outlet being closed by a closure element that is force fitted in the composition outlet of the reservoir. The device includes a mechanical opening system that co-operates with the closure element so as to expel it mechanically from its closed position while the (Continued)

device is actuated. The closure element is an element that is not spherical, including a rounded portion, in particular a hemi-spherical portion, that faces towards the inside of the reservoir in the closed position.

2 Claims, 1 Drawing Sheet

(52) U.S. Cl.
CPC ......... *A61M 15/0061* (2014.02); *B05B 11/06* (2013.01); *A61M 2202/04* (2013.01); *A61M 2202/064* (2013.01); *A61M 2205/073* (2013.01)

(58) Field of Classification Search
CPC . A61M 2202/073; B05B 11/06; B05B 11/062
USPC ........................................ 222/389, 216, 136
See application file for complete search history.

(56) References Cited

U.S. PATENT DOCUMENTS

| | | | | |
|---|---|---|---|---|
| 8,210,167 B2* | 7/2012 | Corbacho | ......... | A61M 15/0028 128/200.21 |
| 2004/0050885 A1* | 3/2004 | Stradella | ........... | A61M 15/0028 222/633 |

FOREIGN PATENT DOCUMENTS

| | | |
|---|---|---|
| FR | 2 775 963 A1 | 9/1999 |
| WO | 91/12895 A1 | 9/1991 |
| WO | 99/46055 A1 | 9/1999 |
| WO | 02/45866 A1 | 6/2002 |

OTHER PUBLICATIONS

International Search Report for PCT/FR2014/051727 dated Sep. 18, 2014 [PCT/ISA/210].

* cited by examiner

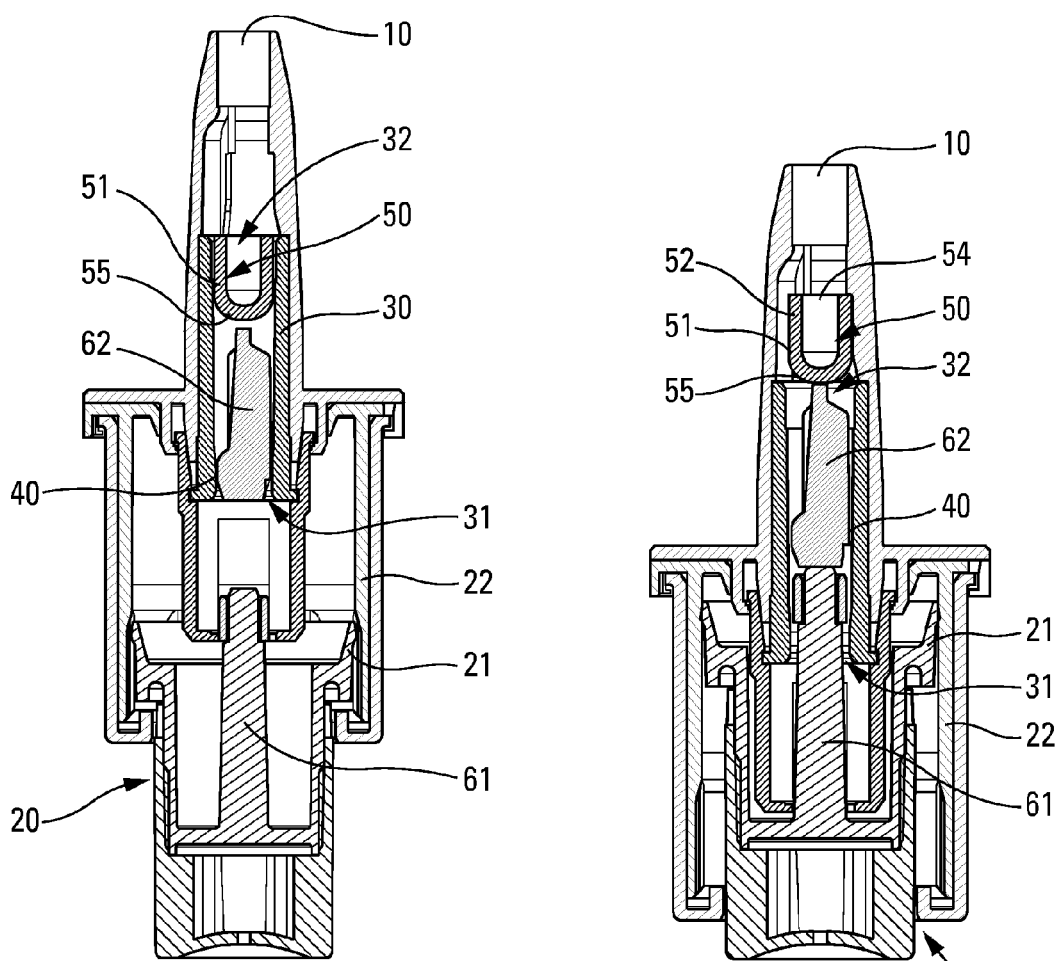
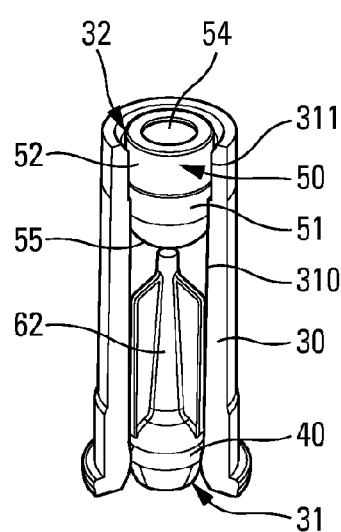
Fig. 1  Fig. 2  Fig. 3

FLUID OR POWDERY PRODUCT DISPENSING DEVICE

The present invention relates to a dispenser device for dispensing a fluid or powder composition, and more particularly it relates to a device for dispensing a dose of a composition contained in a reservoir, by means of a flow of air under pressure.

Document WO 99/46055 discloses such a device in which a spherical closure element, which closes the outlet of the reservoir, is expelled by the flow of air created by an air expeller. In order to use a dispenser device more particularly for dispensing powder, the air pressure necessary for actuating the device must be sufficiently high to guarantee that the dose is dispensed completely, and that it is broken up, if that is necessary. In the above-mentioned device, the air pressure necessary to actuate the device is determined by the resistance opposed by the ball in order to be expelled. That resistance is relatively difficult to control and to predetermine since it depends on the friction between the ball and its cylindrical seat in which it is engaged for the purpose of closing said reservoir in leaktight manner. Consequently, it may be necessary to minimize the interference between the sphere and its cylindrical seat, and obviously that might spoil the effectiveness of the closure. Furthermore, it may be necessary to minimize the depth and the positioning of the sphere in its seat so as to make it easier to expel. It may also be necessary to provide air pressure that is relatively high, which is not always easy to achieve by means of a pump system or of a bellows system, in particular when the air expellers are actuated manually by the patient. Furthermore, dispensing, i.e. expelling the ball from its seat, may take place at different positions along the stroke of the pump or of the bellows of the air expeller, such that the precise moment of dispensing the composition cannot always be predetermined in exact manner. Finally, there is a limit on the materials that can be chosen for the sphere and for its seat.

Document WO 02/45866 describes a device in which a closure ball is expelled mechanically by a rod that is secured to an air expeller. That embodiment presents several drawbacks. Thus, the use of a spherical closure element, such as a ball, provides leaktight sealing at rest, only along a sealing line, namely the outside diameter of the ball. That may present a risk of sealing being lost, and requires the ball and the channel in which said ball is jammed to be dimensioned accurately. Furthermore, since plastic balls need to be ground to shape, there is a risk of metal particles coming from the tools for grinding the balls.

Documents WO 91/12895 and EP 1 321 160 describe other prior-art devices.

An object of the present invention is to provide a fluid or powder dispenser device that does not have the above-mentioned drawbacks.

An object of the present invention is thus to provide a fluid or powder dispenser device in which the closure element guarantees, on every occasion, leaktight closure of the reservoir at rest.

Another object of the present invention is to provide a fluid or powder dispenser device of the above-mentioned type that is simple and inexpensive to manufacture and to assemble.

The present invention thus provides a dispenser device for dispensing a fluid or powder composition, the dispenser device including a dispenser outlet, an air expeller for generating a flow of air while the device is being actuated, and at least one reservoir that contains a single dose of composition, said reservoir including an air inlet that is connected to said air expeller, and a composition outlet that is connected to said dispenser outlet, said air inlet including a composition retainer member for retaining the composition in the reservoir until the composition is dispensed, and said composition outlet being closed by a closure element that is force fitted in the composition outlet of the reservoir, said device including a mechanical opening system that co-operates with said closure element so as to expel it mechanically from its closed position while the device is being actuated, the closure element being an element that is not spherical, said closure element including a rounded portion, in particular a hemi-spherical portion, that faces towards the inside of the reservoir in the closed position.

Advantageously, said closure element includes a cylindrical portion having at least one portion that co-operates with said composition outlet to define a peripheral sealing surface.

Advantageously, said closure element includes a hollow cylindrical axial sleeve that is open at one axial end, and that is closed at the other axial end by a rounded portion, in particular a hemi-spherical portion.

Advantageously, at least one portion of said mechanical opening system is secured to said air expeller.

Advantageously, said mechanical opening system comprises a first rod portion that is secured to said air expeller, and a second rod portion that is secured to said composition retainer member.

Advantageously, said air expeller includes a piston that slides in an air chamber.

These characteristics and advantages, and others, appear more clearly from the following detailed description of an advantageous embodiment, given by way of non-limiting example, and with reference to the accompanying drawing, in which:

FIG. 1 is a diagrammatic section view of a fluid or powder dispenser device in an advantageous embodiment of the present invention, in its rest position;

FIG. 2 is a view similar to the view in FIG. 1, in the actuated position; and

FIG. 3 is a diagrammatic cut-away view in perspective showing a fluid or powder reservoir in an advantageous embodiment of the present invention.

The present invention relates more particularly to a device of the type disclosed in document WO 02/45866. That document describes the general operation of the device.

However, it should be understood that the present invention is not limited to that type of device, but, on the contrary, applies to any type of fluid and powder dispenser device that includes a reservoir closed by a closure element, the contents of the reservoir needing to be expelled by a flow of air.

The figures show an advantageous embodiment of the invention. The device includes a reservoir 30 including an air inlet 31 and a composition outlet 32. The air inlet 31 of the reservoir is connected to an air expeller 20, and the composition outlet 32 of the reservoir is connected to a dispenser outlet 10 of the device. The composition outlet 32 is closed by a closure element 50 that is force fitted in said composition outlet 32. The air inlet 31 is provided with a composition retainer member 40 that is suitable for retaining the composition in the reservoir before the device is actuated. The air expeller 20 is actuated manually by the user, and is suitable for creating a flow of air that passes through the reservoir 30 so as to deliver the composition that it contains towards the dispenser outlet 10.

The device includes a mechanical opening system 61, 62 that is preferably secured to the air expeller 20, i.e. it is actuated simultaneously with said air expeller 20 being actuated, and that is suitable for co-operating with said closure element 50 so as to expel it mechanically from its closed position while the device is being actuated. In the embodiment shown in FIGS. 1 and 2, the mechanical opening system includes a set of rods 61, 62, having a first rod portion 61 that is secured to the air expeller 20, and a second rod portion 62 that is thrust by said first rod portion 61 when the device is actuated. At the end of their actuation stroke, i.e. in the dispensing position, the set of rods 61, 62 co-operate with the closure element 50 so as to expel it mechanically from its closed position.

The composition retainer member 40 may advantageously be made integrally with the second rod portion 62. Thus, the composition retainer member 40 can be made in leaktight and airtight manner before the device is actuated, the air pressure created by the air expeller 20 penetrating into the reservoir 30 only when said retainer member 40 is moved together with the second rod portion 62, by being thrust by the first rod portion 61.

The composition retainer member 40 is advantageously made in the form of a rigid disk that is extended inside the reservoir by the second rod portion 62. The second rod portion 62 is preferably made with a central portion that may be cone shaped or of a shape that is approximately similar, and a plurality of side fins, there being three in the embodiment in FIG. 3. In particular, the fins guide the second rod portion 62 in the reservoir body during actuation. Advantageously, said disk forming the powder retainer member is force fitted in the reservoir body. In a variant, said disk may be fastened, e.g. heat-sealed, to the reservoir body. This guarantees proper sealing at rest, and requires said seal to be broken at the moment of actuation.

The air expeller shown in FIGS. 1 and 2 includes a piston 21 that slides in an air chamber 22, the piston 21 being actuated manually by the user. The presence of the rod, and in particular of the first rod portion 61, may provide guidance for said piston 21, and this makes it easier to actuate, requiring said piston to move axially inside the chamber 22.

In the invention, the closure element 50 is not spherical. This improves sealing and avoids there being any metal particles associated with grinding balls made of plastics material.

Preferably, the closure element 50 includes a cylindrical portion 51 that co-operates with said composition outlet 32 to define a peripheral sealing surface. Sealing is thus formed not along a sealing line, as with a spherical ball, but over a cylindrical surface.

The embodiment in the figures shows an advantageous closure element 50 that includes a hollow axial cylindrical sleeve. At one axial end, which is the end facing towards the inside of the reservoir 30 in the closed position, the closure element 50 includes a rounded portion 55, in particular a hemi-spherical portion, so as to make it easier for the composition to pass towards the dispenser outlet 10 during actuation. At the other axial end 54, the hollow sleeve may advantageously be open. This embodiment gives a degree of flexibility to the closure element 50, which makes it easier to put it into place and makes it possible, in part, to compensate for manufacturing dimensional tolerances, so as to guarantee leaktight closure in the closed position.

As can be seen in FIG. 3, the end of the reservoir body 30 that defines the composition outlet 32 may include an axial edge portion 311 of diameter that is a little bigger than the portion 310 that co-operates in leaktight manner with the closure element 50 in the closed position. The hollow axial sleeve of the closure element 50 may also include an axial edge portion 52 of outside diameter that is a little smaller than the outside diameter of the cylindrical portion 51 that co-operates in leaktight manner with the reservoir body in the closed position. In particular, this makes it easier to put the closure element 50 into place.

Although described mainly in connection with a powder composition, the present invention also applies to dispensing liquids.

The present invention is described above with reference to an advantageous embodiment, but naturally any modification could be applied thereto by a person skilled in the art, without going beyond the ambit of the present invention, as defined by the accompanying claims.

The invention claimed is:

1. A dispenser device for dispensing a fluid or powder composition, the dispenser device including a dispenser outlet, an air expeller for generating a flow of air while the device is being actuated, and at least one reservoir that contains a single dose of a composition, said reservoir including an air inlet that is connected to said air expeller, and a composition outlet that is connected to said dispenser outlet, said air inlet including a composition retainer member for retaining the composition in the reservoir until the composition is dispensed, and said composition outlet being closed by a closure element that is force fitted in the composition outlet of the reservoir, said device including a mechanical opening system that includes a set of rods that, at the end of an actuation stroke, co-operate with said closure element so as to expel it mechanically from a closed position while the device is being actuated, said set of rods comprises a first rod portion that is secured to said air expeller, and a second rod portion that is secured to said composition retainer member, the closure element includes a hollow cylindrical axial sleeve that co-operates with said composition outlet to define a peripheral sealing surface, said hollow cylindrical axial sleeve being open at one axial end, and closed at the other axial end by a rounded portion, being a hemi-spherical portion, said rounded portion facing towards an inside of the reservoir in the closed position.

2. The device according to claim 1, wherein said air expeller includes a piston that slides in an air chamber.

* * * * *